United States Patent [19]

Kasai et al.

[11] Patent Number: 5,030,721
[45] Date of Patent: Jul. 9, 1991

[54] NOVEL N-ACETYL-β-D-GLUCOSAMINE DERIVATIVES AND A PROCESS FOR PRODUCTION THEREOF AS WELL AS APPLICATION TO REAGENTS FOR ASSAYING N-ACETYL-β-D-GLUCOSAMINIDASE ACTIVITY

[75] Inventors: Kouichi Kasai; Shoichi Tokutake; Nobuyuki Yamaji, all of Noda, Japan

[73] Assignee: Kikkoman Corporation, Noda, Japan

[21] Appl. No.: 305,096

[22] Filed: Feb. 2, 1989

[30] Foreign Application Priority Data

Feb. 18, 1988 [JP] Japan .................................. 63-33994

[51] Int. Cl.$^5$ ........................................... C07H 17/00
[52] U.S. Cl. ........................................ 536/4.1; 435/4; 435/7; 435/16; 435/18; 514/893; 536/17.3; 536/17.7; 536/18.5; 544/102
[58] Field of Search ...................... 536/4.1, 17.3, 17.7, 536/18.5; 544/102; 514/893; 435/4, 7, 16

[56] References Cited

U.S. PATENT DOCUMENTS 4,737,466 4/1988 Klein et al. .................... 436/115
4,954,630 9/1990 Klein et al. .................... 530/802

FOREIGN PATENT DOCUMENTS 1257253 7/1989 Canada .
3411574 10/1985 Fed. Rep. of Germany .

OTHER PUBLICATIONS

Dance et al., "B-Galactosidase, B-Glucosidase and N-Acetyl-B-Glucosaminidase in Human kidney," Clinica Chimica Acta, 24:189-197 (1969).
Li et al., "A-Mannosidase, B-N-Acetylhexosaminidase, and B-Calactosidase from Jack Bean Meal," Methods Enzymol., 28:702-713, (1972).
Noto et al., "Simple, Rapid Spectrophotometry of Urine N-Acetyl-B-D-Glucosaminidase, with Use of a New Chromogenic Substrate,"Clin. Chem., 29:1713-1716, (1983).

Primary Examiner—Ronald W. Griffin
Attorney, Agent, or Firm—Banner, Birch, McKie & Beckett

[57] ABSTRACT

Novel N-acetyl-β-D-glucosamine derivatives represented by the following formula:

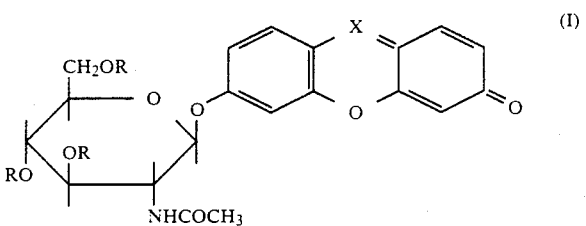

wherein R represents a hydrogen atom or an acyl group; and X represents a nitrogen atom or an oxide of nitrogen, are disclosed. The glucosamine derivatives are useful for determination of N-acetyl-β-D-glucosaminidase in body fluids as an index of renal diseases.

10 Claims, No Drawings

F I G. 1
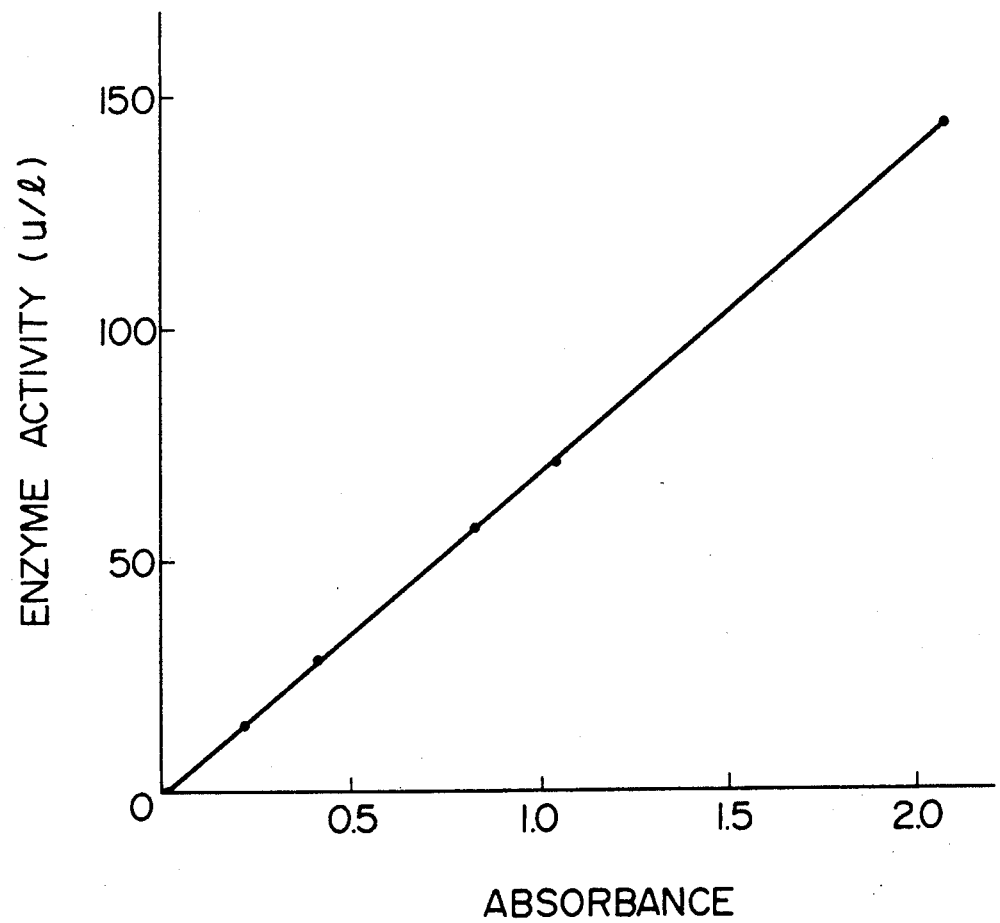

NOVEL N-ACETYL-β-D-GLUCOSAMINE DERIVATIVES AND A PROCESS FOR PRODUCTION THEREOF AS WELL AS APPLICATION TO REAGENTS FOR ASSAYING N-ACETYL-β-D-GLUCOSAMINIDASE ACTIVITY

BACKGROUND OF THE INVENTION

1. Field of the Invention

The present invention relates to novel N-acetyl-β-D-glucosamine derivatives, a process for preparation thereof, a method for determining N-acetyl-β-D-glucosaminidase activity and application to reagents for assaying N-acetyl-β-D-glucosaminidase activity.

2. Description of the Prior Art

N-Acetyl-β-D-glucosaminidase (hereinafter simply referred to as NAGase) is one of enzymes in lysosome distributed in the kidney tubular epithelium in large quantities and participates in decomposition of glycoprotein or mucopolysaccharide. It is recognized that urinary NAGase increases in various renal diseases such as acute renal deficiency, glomerulonephritis, etc. or in postoperative kidney. It is also recognized that NAGase increases in the case of diabetes not only in urine but in serum. As an aid of diagnosis and course observation of various renal diseases and also as an index of studies of a drug on renal toxicity, attention has been brought to assay for NAGase in clinical field and animal experiments.

As substrates for determining NAGase activity hitherto known, there are, for example, p-nitrophenyl-N-acetyl-β-D-glucosaminide [Methods Enzymol., 28, 702 (1972)] and 4-methylumbelliferyl-N-acetyl-β-D-glucosaminide [Clinica. Chemica. Acta., 24, 189 (1969)] and m-cresolsulfonephthaleinyl-N-acetyl-β-D-glucosaminide [Clin. Chem., 29, 1713 (1983)].

In case that p-nitrophenyl-N-acetyl-β-D-glucosaminide described above is used as substrate for determination of NAGase activity, however, the substrate encounters defects that it is affected by yellow substances in urine to increase blank data, since the formed p-nitrophenol is measured at a wavelength at about 400 nm and measurement accuracy is seriously reduced, etc. 4-Methylumbelliferyl-N-acetyl-β-D-glucosaminide involves defects that it is also affected in blank data and requires special devices such as a fluorophotometer, etc. Furthermore, in the case of using p-nitrophenyl-N-acetyl-β-D-glucosaminide and m-cresolsulfonephthaleinyl-N-acetyl-β-D-glucosaminide, aglycone formed by the action of enzyme is colorimetrically determined in such a highly alkaline pH region of the reaction solution as approximately 10 to 11 so that the enzyme reaction must be discontinued; hence, the substrate is disadvantageous in that continuous determination of the enzyme activity is performed only with extreme difficulty.

SUMMARY OF THE INVENTION

In order to improve the defects of the prior art, the present inventors have made extensive investigations and as a result, they have newly presented novel N-acetyl-β-D-glucosamine derivatives and found that the derivatives are extremely useful as reagents for determination of NAGase activity.

BRIEF DESCRIPTION OF THE DRAWINGS

In the accompanied drawings, FIG. 1 is a graph showing relationship between determination of NAGase activity and absorbancy of the formed dye at a wavelength of 570 nm in Example 5.

DETAILED DESCRIPTION OF THE INVENTION

Figure 2:
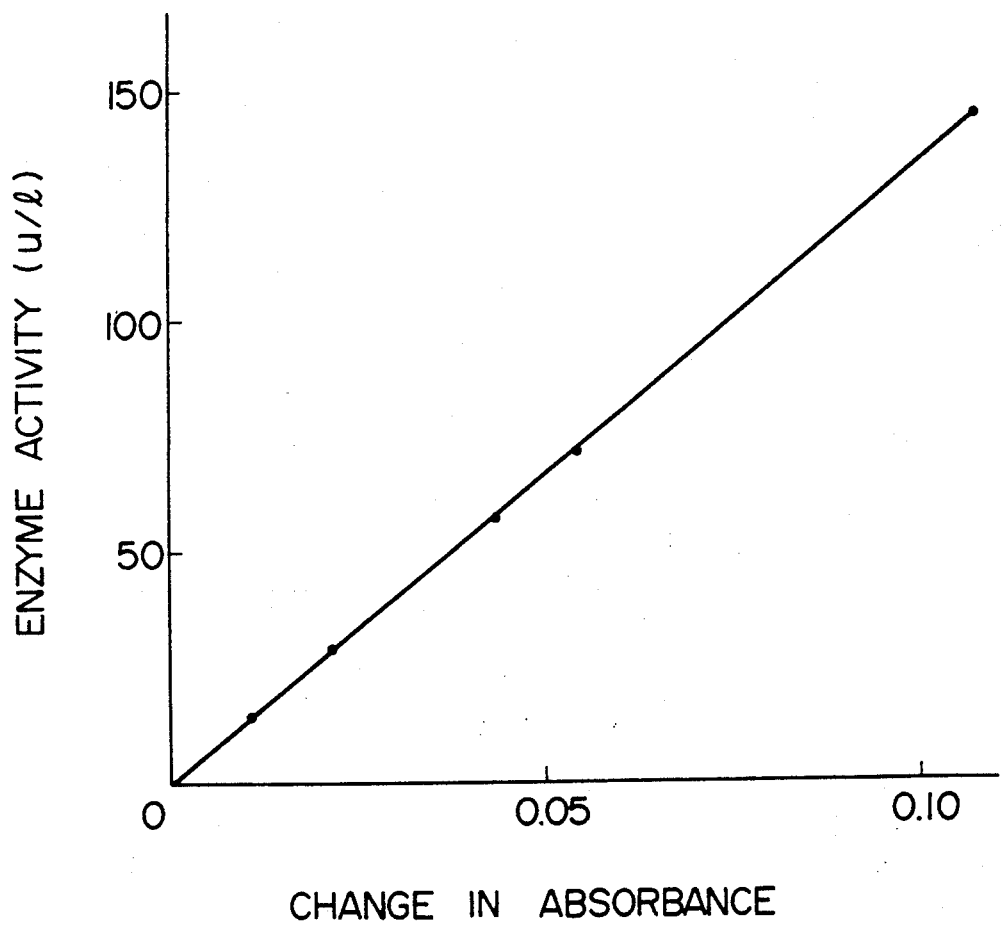
FIG. 2 is a graph showing relationship between determination of NAGase activity and change in absorbancy of formed dye at a wavelength of 600 nm in Example 6. In the figures, linear lines indicate calibration curves, respectively.

The present invention is concerned with N-acetyl-β-D-glucosamine derivatives represented by the following formula:

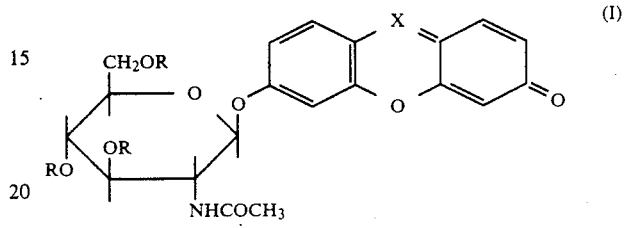

wherein R represents a hydrogen atom or an acyl group; and X represents a nitrogen atom or an oxide of nitrogen.

Examples of the N-acetyl-β-D-glucosamine derivative of formula I include compounds described below: resorufinyl-N-acetyl-β-D-glucosaminide [R=H, X=N], resazurinyl-N-acetyl-β-D-glucosaminide [R=H, X=N→O], resorufinyl-2,3,4,6-tetraacetyl-β-D-glucosaminide [R=COCH₃, X=N], resazurinyl-2,3,4,6-tetraacetyl-β-D-glucosaminide [R=COCH₃, X=N→O], etc.

The N-acetyl-β-D-glucosamine derivative of formula I can be prepared by reacting a halogeno-N-acetyl-D-glucosamine derivative represented by the following formula:

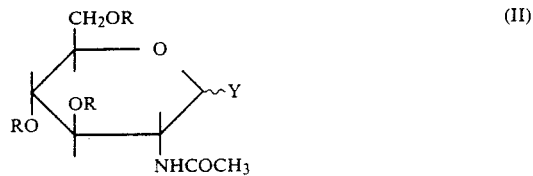

wherein R represents an acyl group and Y represents a halogen atom, with a compound represented by the following formula:

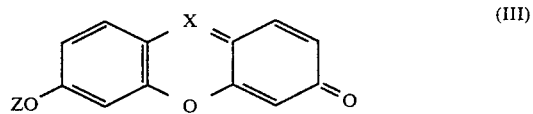

wherein X represents a nitrogen atom or an oxide of nitrogen and Z represents a hydrogen atom, an organic ammonium group or an alkali metal atom, if necessary and desired, followed by de-O-acylation.

Compound II can be prepared, for example, by reacting commercially available N-acetyl-D-glucosamine with acetyl chloride [J. Org. Chem., 27, 1794 (1962)]. Examples of Compound II are 1-chloro-1-deoxy-2,3,4,6-tetraacetyl-α-D-glucosamine and the like.

Compound III may be one that is commercially available or may also be synthesized by a suitable method. Examples of Compound III include resorufine [7- hydroxy-3H-phenoxazin-3-one], resazurine [7-hydroxy-3H-phenoxazin-3-one 10-oxide] and sodium salts thereof, triethylammonium salts thereof, etc. Compound III is generally used in a amount of 1 to 10 molar equivalents, preferably 2 to 5 molar equivalents, per mole of Compound II.

As the solvent, mention may be made of ketones, e.g., acetone, methyl ethyl ketone, etc.; nitriles, e.g., acetonitrile, etc.; halogenated hydrocarbons, e.g., dichloromethane, chloroform, dichloroethane, etc.; dimethyl formamide (DMF), dimethylacetamide (DMA), dimethylsulfoxide (DMSO), hexamethylphosphoramide (HMPS), etc. These solvents may be used in combination but particularly preferred is acetonitrile. The solvent is generally used in an amount of 5 to 500 times, preferably 20 to 200 times, based on the weight of Compound II.

Examples of the catalyst include silver salts, e.g., $Ag_2O$, $AgClO_4$, $AgNO_3$, $Ag_2CO_3$, etc.; mercury salts, e.g., HgO, $Hg(CN)_2$, etc.; cadmium salts, e.g., $CdCO_3$; tertiary amines, e.g., triethylamine, tributylamine, etc. These catalysts may be used in combination but preferred is $Ag_2O$. The catalyst is used generally in an amount of 1 to 10 molar equivalents, preferably 2 to 5 molar equivalents, per mole of Compound II.

The reaction temperature and reaction time may vary depending upon kind of Compound II, Compound III, solvent and catalyst but the reaction is continuously performed generally at 20° to 60° C. for 1 to 60 hours.

By reacting the thus obtained Compound I wherein R is an acyl group with a base to thereby remove the O-acyl group, Compound I wherein R is a hydrogen atom (Compound I') can be obtained. As the base, there are alkali metal salts, for example, KOH, $K_2CO_3$, NaOH, $NaCO_3$, etc.; alkali metal alcoholates, for example, sodium methylate, sodium phenolate, etc.; and ammonia and the like. Of these, anhydrous potassium carbonate is particularly preferred. The base is generally used in an amount of 0.1 to 5 molar equivalents, preferably 0.2 to 1 molar equivalents, per mole of Compound I.

Compound I wherein R is a hydrogen atom can be used for determination of NAGase activity.

Accordingly, the present invention is also directed to a reagent for determination of NAGase activity comprising the N-acetyl-β-D-glucosamine derivative represented by the following formula:

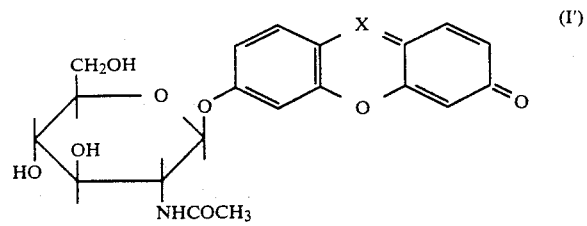

wherein X represents a nitrogen atom or an oxide of nitrogen, and a buffer.

The system that is advantageous for quantitative determination contains 1 to 20 mM of the N-acetyl-β-D-glucosamine derivative and 2 to 100 mM of buffer (pH 3.5 to 6.5). As the buffer, phosphates, acetates, carbonates, Tris-(hydroxymethyl)-aminomethane, borates, citrates, dimethyl glutamates, etc. are used. If necessary and desired, glycerine, bovine serum albumin, Triton X 100, etc., crown ethers, cyclodextrins or glycols, etc. may also be added as dissolution aids or stabilizers to the system.

The reagent of the present invention may be present as a dry element or in a dissolved form; alternatively, the reagent may also be impregnated with a thin layer carrier, for example, a sheet, immersible paper, etc. By the use of this reagent, the activity of NAGase contained in various samples can be determined accurately in a simple manner with high sensitivity.

Next, the method for determination of NAGase activity according to the present invention is described below.

First, approximately 1 to 20 mM, preferably 1 to 5 mM of the N-acetyl-β-D-glucosamine derivative (I') is added to a sample containing NAGase. A buffer is further added thereto and the mixture is subjected to enzyme reaction at 30° to 60° C. for at least 3 minutes, preferably 5 to 120 minutes, at pH of 3.5 to 6.5. With respect to the formed aglycon (resorufines), their absorbancy values are continuously or discontinuously measured directly with a spectral photometer or a fluorophotometer. By comparing to absorbancy values of standard NAGase previously measured, NAGase activity in the sample can be calculated.

The NAGase-containing sample used in the present invention may be any sample as far as it contains NAGase. Specific examples include a culture solution of microorganism, a plant extract, a body fluid of animal, urine, tissue and an extract thereof, etc.

Examples of the buffer are phosphates, acetates, carbonates, Tris-(hydroxymethyl)-aminomethane, borates, citrates, dimethyl glutarates, etc. If necessary, pretreatment is performed or an oxidizing agent is added to minimize the effect of reducible substances.

According to the method for determination of the present invention NAGase activity can be determined accurately in a simple manner by means of automated analysis, manual analysis, dry analysis, etc., without being affected by glucose, billirubin, hemoglobin and the like contained in a sample.

Hereinafter the present invention is described in detail by referring to the examples.

EXAMPLE 1

Preparation of resorufinyl-2,3,4,6-tetraacetyl-β-D-glucosaminide:

1-Chloro-1-deoxy-2,3,4,6-tetraacetyl-β-D-glucosamine, 2.0 g (5.5 mmols), was dissolved in 250 ml of acetonitrile and 3.5 g (16.4 mmols) of resorufine and 3.8 g (16.4 mmols) of silver oxide ($Ag_2O$) were added to the solution. The mixture was reacted at 40° C. for 10 hours while stirring. Then, unreacted $Ag_2O$ was filtered off. After acetonitrile in the filtrate was distilled off, the residue was purified by silica gel chromatography. The fraction eluted with a chloroform-acetonitrile mixture (volume ratio, 6:4) was recrystallized from a chloroform-diethyl ether mixture to give 1221 mg (2.25 mmols, 41.2%) of resorufinyl-2,3,4,6-tetraacetyl-β-D-glucosaminide.

Melting point: 208.0°-210.0° C. (decomposed)

UV and visible absorption spectra (MeOH): Maximum absorption wavelength [λmax]=450 (ε=19200), 375, 248 nm IR absorption spectra (KBr): 3480 (sh), 3300, 1745, 1660, 1605, 1565, 1510 cm$^{-1}$ Nuclear magnetic resonance spectra (200 MHz): (DMSO-d$_6$): δ(ppm) 8.04 (1 H, d, J=8.8 Hz, NH), 7.79

(1 H, d, J=8.8 Hz), 7.53 (1 H, d, J=10.0 Hz), 7.20 (1 H, d, J=2.4 Hz), 7.07 (1 H, dd, J=8.8 Hz, 2.4 Hz), 6.80 (1 H, dd, J=10.0 Hz, 1.7 Hz), 6.25 (1 H, d, J=1.7 Hz), 5.56 (1 H, d, J=8.8 Hz), 5.25 (1 H, brt, J=9.8 Hz), 4.95 (1 H, brt, J=9.8 Hz), 4.00–4.40 (4 H, m), 2.03 (3 H, s), 2.01 (3 H, s), 1.96 (3 H, s), 1.79 (3 H, s)

EXAMPLE 2

Preparation of resorufinyl-N-acetyl-$\beta$-D-glucosaminide:

Resorufinyl-2,3,4,6-tetraacetyl-$\beta$-D-glucosaminide, 434 mg (0.8 mmols), was dissolved in a mixture of methanol (40 ml)-acetonitrile (20 ml) and 28 mg (0.2 mmol) of anhydrous potassium carbonate was added to the solution. The mixture was reacted at room temperature for 1 hour while stirring. Then, the reaction mixture was allowed to stand at 5° C. for an hour and the precipitated crystals were taken out by filtration. The obtained crystals were recrystallized from methanol to give 333 mg (0.08 mmol, 100.0%) of resorufinyl-N-acetyl-$\beta$-D-glucosaminide.

Melting point: 195.0°–198.0° C. (decomposed)

UV and visible absorption spectra (MeOH): Maximum absorption wavelength [$\lambda$max]=450 ($\epsilon$=18500), 382, 349 nm IR absorption spectra (KBr): 3380 (sh), 3250, 1640 (sh), 1600, 1560, 1505 cm$^{-1}$ Nuclear magnetic resonance spectra (200 MHz): (DMSO-d$_6$): $\delta$(ppm) 7.76 (2 H, d, J=8.8 Hz), 7.52 (1 H, d, J=10.0 Hz), 7.08 (1 H, d, J=2.4 Hz), 7.02 (1 H, dd, J=8.8 Hz, 2.4 Hz), 6.79 (1 H, dd, J=10.0 Hz, 2.0 Hz), 6.26 (1 H, d, J=2.0 Hz), 5.20 (1 H, d, J=8.3 Hz), 5.03 (2 H, brt, J=5.9 Hz), 4.55 (1 H, brt, J=5.6 Hz), 3.10–3.80 (6 H, m), 1.82 (3 H, s)

EXAMPLE 3

Preparation of resazurinyl-2,3,4,6-tetraacetyl-$\beta$-D-glucosaminide

1-Chloro-1-deoxy-2,3,4,6-tetraacetyl-$\alpha$-D-glucosamine, 1.5 g (4.1 mmols), was dissolved in 200 ml of acetonitrile and 2.8 g (12.2 mmols) of resazurine and 2.8 g (12.1 mmols) of silver oxide (Ag$_2$O) were added to the solution. The mixture was reacted at room temperature for 30 hours while stirring. Then, unreacted Ag$_2$O was filtered off. After acetonitrile in the filtrate was distilled off, the residue was purified by silica gel chromatography. The fraction eluted with a chloroform-acetonitrile mixture (volume ratio, 6:4) was recrystallized from a chloroform-diethyl ether to give 840 mg (1.51 mmols, 36.7%) of resazurinyl-2,3,4,6-tetraacetyl-$\beta$-D-glucosaminide.

Melting point: 220.0°–221.0° C. (decomposed)

UV and visible absorption spectra (MeOH): Maximum absorption wavelength [$\lambda$max]=520 ($\epsilon$=14600), 489 ($\epsilon$=14600), 375 (sh), 358, 348, 270 nm IR absorption spectra (KBr): 3480 (sh), 3320, 1740, 1660, 1630, 1600, 1540 cm$^{-1}$ Nuclear magnetic resonance spectra (200 MHz): (CDCl$_3$): $\delta$(ppm) 8.13 (1 H, d, J=10.0 Hz), 8.01 (1 H, d, J=10.0 Hz), 7.03 (1 H, d, J=2.0 Hz), 7.01 (1 H, dd, J=10.0 Hz, 2.0 Hz), 6.74 (1 H, dd, J=10.0 Hz, 2.0 Hz), 6.22 (1 H, d, J=2.0 Hz), 6.15 (1 H, d, J=8.1 Hz, NH), 5.52 (1 H, d, J=8.3 Hz), 5.49 (1 H, brt, J=10.0 Hz), 5.14 (1 H, brt, J=9.8 Hz), 4.15–4.35 (3 H, m), 3.95–4.05 (1 H, m) 2.10 (3 H, s), 2.08 (3 H, s), 2.07 (3 H, s), 1.97 (3 H, s)

EXAMPLE 4

Preparation of resazurinyl-N-acetyl-$\beta$-D-glucosaminide

Resazurinyl-2,3,4,6-tetraacetyl-$\beta$-D-glucosaminide, 447 mg (0.8 mmols), was dissolved in a mixture of methanol (40 ml)-acetonitrile (20 ml) and 28 mg (0.2 of anhydrous potassium carbonate was added to the solution. The mixture was reacted at room temperature for 1 hour while stirring. Then, the reaction mixture was allowed to stand at 5° C. for an hour and the precipitated crystals were taken out by filtration. The obtained crystals were recrystallized from methanol to give 154 mg (0.36 mmol, 44.5%) of resazurinyl-N-acetyl-$\beta$-D-glucosaminide.

Melting point: 150.5°–153.0° C. (decomposed)

UV and visible absorption spectra (MeOH): Maximum absorption wavelength [$\lambda$max]=522 ($\epsilon$=14400), 490 ($\epsilon$=14400), 379 (sh), 359, 349, 270 nm IR absorption spectra (KBr): 3380 (sh), 3250, 1650 (sh), 1630, 1600, 1545, 1470 cm$^{-1}$ Nuclear magnetic resonance spectra (200 MHz): (DMSO-d$_6$): $\delta$(ppm) 8.07 (1 H, d, J=9.3 Hz), 7.98 (1 H, d, J=10.0 Hz), 7.77 (1 H, d, J=8.8 Hz, NH), 7.17 (1 H, d, J=2.0 Hz), 7.04 (1 H, dd, J=9.3 Hz, 2.0 Hz), 6.67 (1 H, dd, J=10.0 Hz, 1.7 Hz), 6.15 (1 H, d, J=1.7 Hz), 5.23 (1 H, d, J=8.8 Hz), 5.03 (2 H, brt, J=5.9 Hz), 4.54 (1 H, brt, J=4.9 Hz), 3.10–3.80 (6 H, m), 1.82 (3 H, s)

EXAMPLE 5

Method A for determining N-acetyl-$\beta$-D-glucosaminidase activity (end-point method)

(1) Preparation of substrate solution

One mmole of resorufinyl-N-acetyl-$\beta$-D-glucosaminide is weighed and 50 mM citrate buffer (pH=5.0) is added to make the whole volume 1 liter, which is made as a substrate solution.

(2) Preparation of standard NAGase solutions

Commercially available NAGase solution having known enzyme activity is diluted with 50 mM citrate buffer (pH=5.0) containing 0.05% bovine serum albumin to several kinds of concentrations, which are made as standard NAGase solutions. (3) Preparation of sample solution A sample, 10 mg, for determination of NAGase activity is accurately weighed and added to 50 mM citrate buffer (pH=5.0) containing 0.05% bovine serum albumin to make the whole volume 100 ml, which is made a sample solution.

(4) Preparation of calibration curve

After 0.5 ml each of standard NAGase solutions having various concentrations is added to 1 ml of substrate solution, the mixture is heated at 37° C. for 15 minutes. Immediately after 2 ml of 200 mM sodium carbonate aqueous solution is added to the mixture, absorbancy is measured at 570 nm. Calibration curve is prepared based on relationship between activities of standard NAGase solutions and their absorbencies.

When NAGase (28.6 U/0.5 ml) made by Sigma Co. is used, its calibration curve is expressed by equation:

$$U = 69.4 \times A - 0.777$$

(wherein U: enzyme activity, U/l, A: absorbancy). The graph is shown in FIG. 1.

(5) Determination of NAGase activity in sample solution

Sample solution, 0.5 ml, is added to 1 ml of substrate solution followed by heating at 37° C. for 15 minutes. Immediately after 2 ml of 200 mM sodium carbonate aqueous solution is added to the mixture, absorbancy is measured at 570 nm. By comparing this absorbancy value to the calibration curve prepared in (4), NAGase activity in the sample solution can be determined.

In case that the enzyme activity value in a sample solution is greater than the measurement limit of the calibration curve (14.3 - 143 U/l), dilution is performed to the corresponding magnification number using 50 mM citrate buffer (pH =5.0) containing 0.05% bovine serum albumin and measurement is again conducted.

EXAMPLE 6

Method B for determining N-acetyl-$\beta$-D-glucosaminidase activity (rate-assay method)

(1) Preparation of substrate solution

One mmole of resazurinyl-N-acetyl-$\beta$-D-glucosaminide is weighed and 50 mM citrate buffer (pH=5.0) is added to make the whole volume 1 liter, which is made as a substrate solution.

(2) Preparation of standard NAGase solutions

Commercially available NAGase solution having known enzyme activity is diluted with 50 mM citrate buffer (pH=5.0) containing 0.05% bovine serum albumin to several kinds of concentrations, which are made as standard NAGase solutions.

(3) Preparation of sample solution

A sample, 10 mg for determination of NAGase activity is accurately weighed and added to 50 mM citrate buffer (pH=5.0) containing 0.05% bovine serum albumin to make the whole volume 100 ml, which is made a sample solution.

(4) Preparation of calibration curve

After 2 ml of substrate solution is heated at 37° C. for 3 minutes, 1 ml each of standard NAGase solutions having various concentrations is added to the substrates solution. The mixture is then heated at 37° C. for 3 minutes. Calibration curve is prepared based on changes in absorbancy at 600 nm for 2 minutes after the heating.

When NAGase (28.6 U/0.5 ml) made by Sigma Co. is used, its calibration curve is expressed by equation:

$$U = 1.33 \times (\Delta A) \times 10^3$$

(wherein U: enzyme activity, U/l, $\Delta A$: change in absorbancy/minute). The graph is shown in FIG. 2.

(5) Determination of NAGase activity in sample solution

After 2 ml of substrate solution is heated at 37° C. for 3 minutes, 1 ml of sample solution is added thereto followed by heating at 37° C. for 3 minutes. Changes in absorbancy at 600 nm are measured for 2 minutes after the heating.

By comparing the change in absorbancy with the calibration curve prepared in (4), NAGase activity in the sample solution can be determined.

In case that the enzyme activity value in a sample solution is greater than the measurement limit of the calibration curve (14.3 - 143 U/l), dilution is performed to the corresponding magnification number using 50 mM citrate buffer (pH=5.0) containing 0.05% bovine serum albumin and measurement is again conducted.

EXAMPLE 7

Reagent A for measurement (1) Composition of reagent:

| Component | Concentration |
| --- | --- |
| Reagent a: | |
| Resorufinyl-N-acetyl-$\beta$-D-glucosaminide | 1.0 mM |
| Citrate buffer (pH = 5.0) | 50.0 mM |
| Purified water | |
| Reagent b: | |
| Sodium carbonate | 200 mM |
| Purified water | |
| Reagent c: | |
| Bovine serum albumin | 0.05% |
| Citrate buffer (pH = 5.0) | 50.0 mM |
| Purified water | |

(2) Method for measurement

First, 10 mg of a sample for measurement is accurately weighed and Reagent c is added thereto to make the whole volume 100 ml, which is made as a sample solution. Then, 0.5 ml of the sample solution is added to 1 ml of Reagent a followed by heating at 37° C. for 15 minutes. Immediately after 2 ml of Reagent b is added to the system, absorbancy is measured at 570 nm. By comparing this absorbancy value to the calibration curve previously prepared, the activity of NAGase in the sample solution can be determined.

In case that the enzyme activity value in the sample solution exceeds the measurement limit of the calibration curve, the sample solution is diluted to the corresponding magnification number using Reagent c and the activity is again measured.

EXAMPLE 8

Reagent B for measurement:

(1) Composition of reagent:

| Component | Concentration |
| --- | --- |
| Reagent a: | |
| Resazurinyl-N-acetyl-$\beta$-D-glucosaminide | 1.0 mM |
| Citrate buffer (pH = 5.0) | 50.0 mM |
| Purified water | |
| Reagent b: | |
| Bovine serum albumin | 0.05% |
| Citrate buffer (pH = 5.0) | 50.0 mM |
| Purified water | |

(2) Method for measurement

First, 10 mg of a sample for measurement is accurately weighed and Reagent b is added thereto to make the whole volume 100 ml, which is made as a sample solution. Then, after 2 ml of Reagent a is heated at 37° C. for 3 minutes, 1 ml of the sample solution is added thereto followed by heating at 37° C. for 3 minutes. Changes in absorbancy at 600 nm for 2 minutes after the heating are measured. By comparing the change in absorbancy to the calibration curve previously prepared, the activity of NAGase in the sample solution can be determined.

In case that the enzyme activity value in the sample solution exceeds the measurement limit of the calibration curve, the sample solution is diluted to the corresponding magnification number using Reagent b and the activity is again measured.

What is claimed is:

1. An N-acetyl-β-D-glucosamine derivative represented by the following formula:

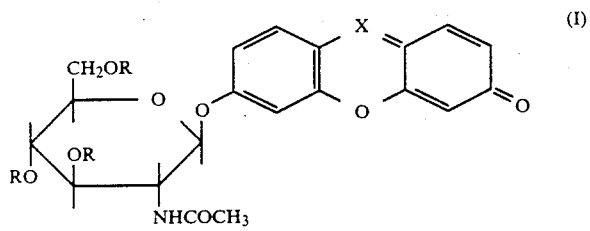

(I)

wherein R represents a hydrogen atom or an acyl group; and X represents a nitrogen atom or an oxide of nitrogen.

2. An N-acetyl-β-D-glucosamine derivative according to claim 1, which is resorufinyl-N-acetyl-β-D-glucosaminide, resazurinyl-N-acetyl-β-D-glucosaminide, resorufinyl-2,3,4,6-tetraacetyl-β-D-glucosaminide or resazurinyl-2,3,4,6-tetraacetyl-β-D-glucosaminide.

3. A process for preparing an N-acetyl-β-D-glucosamine derivative represented by the following formula:

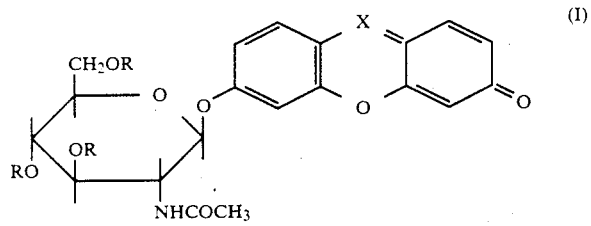

(I)

wherein R represents a hydrogen atom or an acyl group; and X represents a nitrogen atom or an oxide of nitrogen, which comprises reacting a halogeno-N-acetyl-D-glucosamine derivative represented by the following formula:

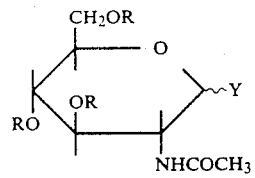

(II)

wherein R represents an acyl group and Y represents a halogen atom, with a resorufines represented by the following formula:

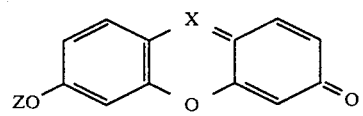

(III)

wherein X represents a nitrogen atom or an oxide of nitrogen and Z represents a hydrogen atom, an organic ammonium group or an alkali metal atom, optionally followed by de-O-acylation.

4. A process for preparing an N-acetyl-β-D-glucosamine derivative according to claim 3, wherein said compound of formula (II) is 1-chloro-1-deoxy-2,3,4,6-tetraacetyl-α-D-glucosamine or 1-bromo-1-deoxy-2,3,4,6-tetraacetyl-u-D-glucosamine.

5. A process for preparing an N-acetyl-β-D-glucosamine derivative according to claim 3, wherein said compound of formula (III) is resorufine [7-hydroxy-3H-phenoxazin-3-one], resazurine [7-hydroxy-3H-phenoxazin-3-one 10-oxide], a sodium salt thereof or a triethylamine salt thereof.

6. A process for preparing an N-acetyl-β-D-glucosamine derivative according to claim 3, wherein said compound of formula (I) is resorufinyl-N-acetyl-β-D-glucosaminide, resazurinyl-N-acetyl-β-D-glucosaminide, resorufinyl-2,3,4,6-tetraacetyl-β-D-glucosaminide or resazurinyl-2,3,4,6-tetraacetyl-β-D-glucosaminide.

7. A reagent for determination of N-acetyl-β-D-glucosaminidase activity comprising as an effective ingredient an N-acetyl-β-D-glucosamine derivative represented by the following formula:

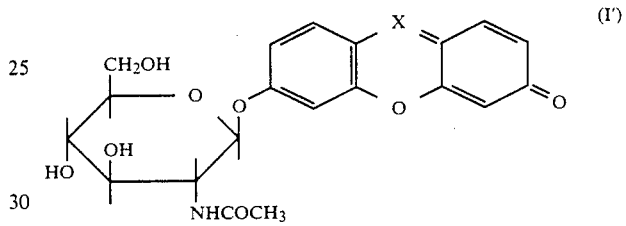

(I')

wherein X represents a nitrogen atom or an oxide of nitrogen.

8. A reagent for determination of N-acetyl-β-D-glucosaminidase activity according to claim 7, wherein said compound of formula (I') is resorufinyl-N-acetyl-β-D-glucosaminide or resazurinyl-N-acetyl-β-D-glucosaminide.

9. A method for determining N-acetyl-β-D-glucosaminidase activity which comprises adding an N-acetyl-β-D-glucosamine derivative represented by the following formula:

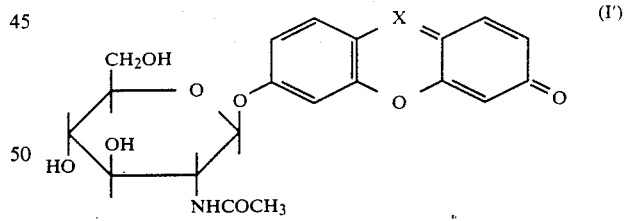

(I')

wherein X represents a nitrogen atom or an oxide of nitrogen, to a sample solution containing N-acetyl-β-D-glucosaminidase and colorimetrically determining the aglycone (resorufines) formed by enzyme reaction directly with a spectrophotometer or fluorometrically determining the same with a fluorophotometer.

10. A method for determining N-acetyl-β-D-glucosaminidase activity according to claim 9, wherein said compound of formula (I') is resorufinyl-N-acetyl-β-D-glucosaminide or resazurinyl-N-acetyl-β-D-glucosaminide.

* * * * *